(12) United States Patent
van Willgenburg

(10) Patent No.: US 10,773,183 B2
(45) Date of Patent: Sep. 15, 2020

(54) SYSTEM AND METHOD FOR SEPARATING HYDROCARBON STREAM

(71) Applicant: SABIC Global Technologies B.V., Bergen op Zoom (NL)

(72) Inventor: Joris van Willgenburg, Geleen (NL)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 117 days.

(21) Appl. No.: 16/312,585

(22) PCT Filed: Jun. 26, 2017

(86) PCT No.: PCT/IB2017/053811
§ 371 (c)(1),
(2) Date: Dec. 21, 2018

(87) PCT Pub. No.: WO2018/002810
PCT Pub. Date: Jan. 4, 2018

(65) Prior Publication Data
US 2020/0254359 A1    Aug. 13, 2020

(30) Foreign Application Priority Data
Jun. 27, 2016   (EP) .................................... 16176454

(51) Int. Cl.
| C10G 7/00 | (2006.01) |
| B01D 3/00 | (2006.01) |
| B01D 3/14 | (2006.01) |
| C07C 7/08 | (2006.01) |
| B01D 3/40 | (2006.01) |

(52) U.S. Cl.
CPC ............. *B01D 3/007* (2013.01); *B01D 3/143* (2013.01); *B01D 3/40* (2013.01); *C07C 7/08* (2013.01); *C10G 7/00* (2013.01)

(58) Field of Classification Search
CPC .................................. B01D 5/0003; C10G 7/00
See application file for complete search history.

(56) References Cited

FOREIGN PATENT DOCUMENTS

| CN | 104744194 A | 7/2015 |

OTHER PUBLICATIONS

S. S. Ding and W. L. Luyben, Control of a Heat-Integrated Complex Distillation Configuration, 20 Ind. Eng. Chem. 1240-1249 (1990).*
European Search Report for European Application No. 17742859.6; Application Filing Date Jun. 26, 2017; dated Feb. 20, 2020, 6 pages.
Chinese Patent No. 104744194; Date of Publication: Jul. 1, 2015; Abstract Only, 1 page.
Ding, Samuel S. et al.; "Control of a Heat-Integrated Complex Distillation Configuration", Ind. Eng. Chem.Res., 1990, vol. 29, pp. 1240-1249.
European Search Report for European Application No. 16176454.3; dated Feb. 1, 2017; 8 pages.
International Search Report for International Application No. PCT/IB2017/053811; dated Oct. 11, 2017; 6 pages.
Written Opinion of the International Search Report for International Application No. PCT/IB2017/053811; dated Oct. 11, 2017; 8 pages.
Young Han Kim, "Energy saving and thermodynamic efficiency of a double-effect distillation column using internal heat integration"; Korean J. Chem. Eng., 2012, vol. 29, pp. 1680-1687.

* cited by examiner

*Primary Examiner* — Randy Boyer
(74) *Attorney, Agent, or Firm* — Cantor Colburn LLP

(57) ABSTRACT

The invention relates to a separation system for separating a feed stream comprising C6+ hydrocarbons, the system comprising: i) a first distillation column for producing a first light stream comprising C6− hydrocarbons and a first heavy stream comprising C7+ hydrocarbons, wherein the first distillation column is operated between a lowest pressure and a highest pressure, ii) a second distillation column for producing a second light stream comprising C6− hydrocarbons and a second heavy stream comprising C7+ hydrocarbons, wherein the second distillation column is operated between a lowest pressure and a highest pressure, wherein the lowest pressure of the second distillation column is higher than the highest pressure of the highest distillation column and iii) a heat exchanger comprising a first reboiler for reboiling a part of the first heavy stream to produce a first boiled heavy stream and a second condenser for condensing the second light stream to produce a second condensed light stream, wherein the first reboiler and the second condenser are arranged such that heat released from the second condenser is used as heat for the first reboiler.

19 Claims, 5 Drawing Sheets

SYSTEM AND METHOD FOR SEPARATING HYDROCARBON STREAM

CROSS REFERENCE TO RELATED APPLICATIONS

This application is a 371 of International Application No. PCT/IB2017/053811, filed Jun. 26, 2017, which claims priority to European Application No. 16176454.3 filed Jun. 27, 2016, both of which are incorporated herein by reference in their entirety.

BACKGROUND

Pyrolysis gasoline—the C5 to C10 hydrocarbon product fraction—consists mainly of aromatics. The non-aromatics are mainly unsaturated hydrocarbons with a high portion of acetylenes and dienes. This stream is unstable and cannot be stored, as the unsaturated components react further, forming polymers and gum. Depending on the downstream processes pyrolysis gasoline is hydrogenated and fractionated in different steps. The most common process route is as follows:
1. Selective hydrogenation of the total gasoline to hydrogenate acetylenes, dienes, and styrene to olefinic compounds. After stabilization and removal of oil, this stream is suitable for use as motor fuel. The reaction is typically controlled in a way that the residual styrene value is ca 0.5%.
2. Fractionation of the effluent of the 1st stage hydrogenation into a C5 cut, a C6–C8 heart cut, and a C9+ cut.
3. The C6–C8 cut is further processed in a 2nd stage hydrogenation step to convert olefins to paraffins and naphthenes and to convert all sulfur to $H_2S$, which is removed from the product in a downstream stripper. This process is necessary to prepare the heart cut for aromatics recovery. The specification is controlled via the bromine number, which is typically 0.5.

Another (commonly applied) method is a first stage hydrogenation, followed by a fractionating through distillation. FIG. 1 schematically illustrates a system for fractionating a hydrocarbon stream by successive distillation.

As shown in FIG. 1, a hydrogenated (from $1^{st}$ stage) stream of pygas (101) is first sent to debutanizer column (C-101), splitting the stream in a C4– cut (102) and a C5+ cut (103). The C5+ cut is sent to depentanizer column C-111, where a C5 fraction (104) is recovered and a C6+ fraction (105). The C6+ fraction is sent to dehexanizer column (C-121), where a C6 fraction is recovered (106) and a C7+ fraction (107) is sent to column C-131, splitting it in a gasoline stream (108) and a heavies stream (109).

The C6 fraction (106) is rich in benzene and can be sent to a benzene extraction plant. It is important for this process that the C6 fraction is free from toluene, since this will be co extracted with the benzene and methyl-cyclohexane.

The separation of hydrocarbon streams consumes a large amount of energy. In particular, it has been calculated that the dehexanizer column has an especially high energy consumption. The result of a computer simulation for the process as shown in FIG. 1 is summarized in Table 1. Mass flow is measured in tons per hour.

TABLE 1

| Stream No. | 101 | 102 | 103 | 104 | 105 | 106 | 107 | 108 | 109 |
|---|---|---|---|---|---|---|---|---|---|
| Mass Flow (t/h) | 70.5 | 0.8 | 69.7 | 10.7 | 58.9 | 31.2 | 27.8 | 13.6 | 14.2 |
| Composition (weight fraction) | | | | | | | | | |
| C4– | 0.010 | 0.867 | 0.000 | 0.003 | 0.000 | 0.000 | 0.000 | 0.000 | 0.000 |
| C5 | 0.164 | 0.133 | 0.165 | 0.907 | 0.029 | 0.055 | 0.000 | 0.000 | 0.000 |
| C6 Aromatics | 0.366 | 0.000 | 0.371 | 0.048 | 0.429 | 0.795 | 0.018 | 0.037 | 0.000 |
| C6 Non-aromatics | 0.069 | 0.000 | 0.070 | 0.042 | 0.075 | 0.140 | 0.002 | 0.004 | 0.000 |
| C7 Aromatics | 0.163 | 0.000 | 0.164 | 0.000 | 0.194 | 0.000 | 0.413 | 0.766 | 0.075 |
| C7 Non-aromatics | 0.020 | 0.000 | 0.020 | 0.000 | 0.024 | 0.008 | 0.041 | 0.080 | 0.004 |
| C8 Aromatics | 0.119 | 0.000 | 0.120 | 0.000 | 0.142 | 0.000 | 0.301 | 0.089 | 0.504 |
| C8 Non-aromatics | 0.004 | 0.000 | 0.004 | 0.000 | 0.005 | 0.002 | 0.009 | 0.015 | 0.002 |
| C9+ | 0.085 | 0.000 | 0.086 | 0.000 | 0.102 | 0.000 | 0.217 | 0.009 | 0.415 |

The calculated heat required for distillation is as follows:
Column; Condenser pressure; reboiler duty; condenser duty
C-101: 7.9 bar atmospher (bara); 2068 kilowatts (kW); 1815 kW
C-111: 2.2 bara; 249 kW; 2002 kW
C-121: 2.4 bara; 8046 kW; 7635 kW
C-132: 0.2 bara; 382 kW; 1661 kW It can be understood that the dehexanizer column (C-121) is the largest energy consumer in this plant, with a heat requirement more than all the other column reboilers of the pygas section together.

Accordingly, it can be desirable to provide a method for separating a hydrocarbon stream between C6 and C7 which is energy efficient.

SUMMARY

Disclosed herein is a system and a method for separating a stream of hydrocarbons comprising C6+ hydrocarbons.

A method for separating a feed stream comprising C6+ hydrocarbons using a separation system for separating a feed stream comprising C6+ hydrocarbons, the system comprises: i) a first distillation column for producing a first light stream comprising C6– hydrocarbons and a first heavy stream comprising C7+ hydrocarbons, wherein the first distillation column is operated between a lowest pressure and a highest pressure, ii) a second distillation column for producing a second light stream comprising C6– hydrocarbons and a second heavy stream comprising C7+ hydrocarbons, wherein the second distillation column is operated between a lowest pressure and a highest pressure, wherein the lowest pressure of the second distillation column is higher than the highest pressure of the highest distillation column, iii) a heat exchanger comprising a first reboiler for reboiling a part of the first heavy stream to produce a first boiled heavy stream and a second condenser for condensing the second light stream to produce a second condensed light stream, wherein the first reboiler and the second condenser are arranged such that heat released from the second condenser is used as heat for the first reboiler, iv) a first condenser for cooling the first light stream to produce a first condensed light stream and v) a second reboiler for reboiling a part of the second heavy stream to produce a second boiled heavy stream, wherein the method comprises the steps of: a) a2) feeding the feed stream to the first distillation column and feeding a part of the first heavy stream to the second distillation column, b) feeding a part of the first heavy stream to the first reboiler and feeding back the first boiled heavy stream to the first distillation column, c) feeding the second light stream to the second condenser and feeding back a part of the second light stream to the second distillation column as reflux and collecting a part of the second condensed light stream from the separation system, d) feeding the first light stream to the first condenser and feeding back a part of the first condensed light stream to the first distillation column as reflux, e) feeding a part of the second heavy stream to the second reboiler and feeding back the second boiled heavy stream to the second distillation column, and f) collecting a part of the first condensed light stream and a part of the second heavy stream from the separation system, wherein the first condensed light stream collected from the separation system comprises at most 500 ppm of toluene and at most 600 ppm of methyl cyclo hexane. These and other features and characteristics are more particularly described below.

BRIEF DESCRIPTION OF THE DRAWINGS

The system and method now further elucidated referring to the drawings in which.

DETAILED DESCRIPTION

Figure 1:
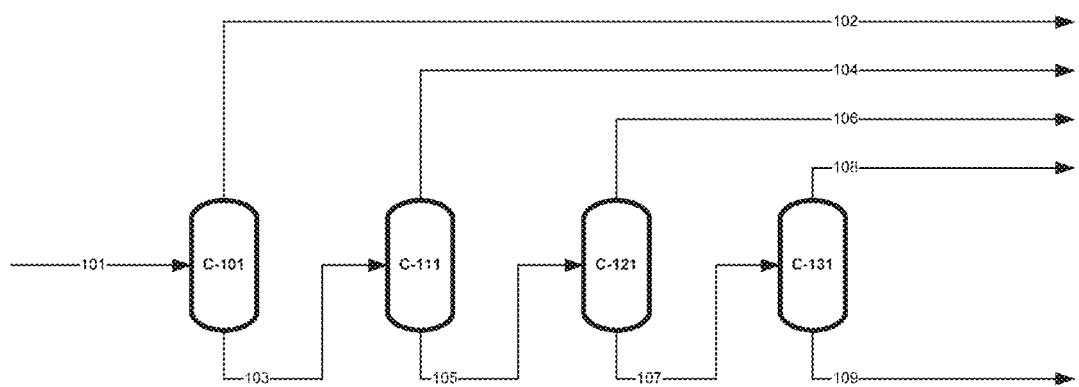
FIG. 1 schematically illustrates a system for fractionating a hydrocarbon stream by successive distillation.

Accordingly, disclosed herein is a separation system for separating a feed stream comprising C6+ hydrocarbons, the system comprising:
i) a first distillation column (C-221; C-321) for producing a first light stream (205; 302) comprising C6− hydrocarbons and a first heavy stream (209,210; 307,309) comprising C7+ hydrocarbons, wherein the first distillation column is operated between a lowest pressure and a highest pressure,
ii) a second distillation column (C-222; C-322) for producing a second light stream (223; 311) comprising C6− hydrocarbons and a second heavy stream (221,227; 320, 318) comprising C7+ hydrocarbons, wherein the second distillation column is operated between a lowest pressure and a highest pressure, wherein the lowest pressure of the second distillation column is higher than the highest pressure of the highest distillation column and
iii) a heat exchanger (H-222; H-322) comprising a first reboiler for reboiling a part (209; 307) of the first heavy stream to produce a first boiled heavy stream (211; 308) and a second condenser for condensing the second light stream (223; 311) to produce a second condensed light stream (226,222; 315,316), wherein the first reboiler and the second condenser are arranged such that heat released from the second condenser is used as heat for the first reboiler.

Also disclosed herein is a method for separating a feed stream comprising C6+ hydrocarbons using the separation system previously described herein, wherein the method comprises the steps of:
a) a1) feeding the feed stream (201) partly (202) to the first distillation column (C-221) and partly (203) to the second distillation column (C-222) and collecting a part (210) of the first heavy stream from the separation system, or
a2) feeding the feed stream (301) to the first distillation column (C-321) and feeding a part (309) of the first heavy stream to the second distillation column (C-322),
b) feeding a part (209; 307) of the first heavy stream to the first reboiler and feeding back the first boiled heavy stream (211; 308) to the first distillation column (C-221; C-321) and
c) feeding the second light stream (223; 311) to the second condenser and feeding back a part (226; 315) of the second light stream to the second distillation column (C-222; C-322) as reflux and collecting a part (222; 316) of the second condensed light stream from the separation system.

It will be appreciated that the steps of the method (a1), b) and c) or a2, b) and c) are not necessary performed successively. Rather, the steps are performed in parallel continuously. It will be further appreciated that the reference numerals used in the claims and the description are used only for the purpose of explanation and the invention is not limited to the embodiments illustrated by the drawings. The present application is based on the realization that the heat released from condensing of a stream can be used as the heat for reboiling of another stream.

A reboiler comprises a part through which a liquid to be reboiled passes and a heating means is required for heating said part. A condenser comprises a part through which a gas to be condensed passes and a cooling means is required for cooling said part. The system disclosed herein comprises an element which works both as a reboiler for one stream and a condenser for another stream. In this element, the reboiler part (first reboiler for reboiling the first heavy stream) works as a cooling means for the condenser part (second condenser for condensing the second light stream), and the condenser part works as a heating means for the reboiler part. Accordingly, additional heating means are not needed for reboiling the first heavy stream or condensing the second light stream, which substantially reduces the overall energy consumption of the system.

The heat released from the second condenser for condensing the second light stream must be equal to the heat required by the first reboiler to reboil the first heavy stream. This is achieved by adjusting the amounts of the feed streams to each of the distillation columns. In the case of the second embodiment as described later, the composition of the feed stream to the second distillation column can also be adjusted. The amount of C6− hydrocarbons in the feed stream to the second distillation column influences the amount of heat released by the second condenser which has to match the heat required by the first reboiler, as described more in detail later.

Further, the temperature at which heat is released from the second condenser must be higher than the temperature at which the heat is required by the first reboiler. This is achieved by setting a desirable pressure difference between the highest pressure of the first distillation column (=the pressure of the first reboiler) and the lowest pressure of the second distillation column (=the pressure of the second condenser).

Preferably, the separation system further comprises iv) a first condenser (H-221; H-321) for cooling the first light stream (205; 302) to produce a first condensed light stream (208,204; 305,306) and v) a second reboiler (H-223; H-323) for reboiling a part (227; 318) of the second heavy stream to produce a second boiled heavy stream (228; 319).

Preferably, the method uses this separation system and the method further comprises the steps of:

d) feeding the first light stream (205; 302) to the first condenser and feeding back a part (208; 305) of the first condensed light stream to the first distillation column (C-221; C-321) as reflux, the first light stream (205; 302) can be passed through the first condenser (H-221; H-321) and output as a first output stream (206; 303). The first output stream (206; 303) can be sent through a first vessel (V-221; V-321) with a second output stream (207; 304) exiting and being sent through a first pump (P-221; P-321). The second output stream (207; 304) can join the first condensed light stream (208, 204; 305, 306).

e) feeding a part (227; 318) of the second heavy stream to the second reboiler (H-223) and feeding back the second boiled heavy stream (228; 319) to the second distillation column (C-221; C-321) and f) collecting a part (204; 306) of the first condensed light stream and a part (221; 320) of the second heavy stream from the separation system.

As used herein, the term "C # hydrocarbons", wherein "#" is a positive integer, is meant to describe all hydrocarbons having # carbon atoms. C # hydrocarbons are sometimes indicated as just "C #". Moreover, the term "C #+ hydrocarbons" is meant to describe all hydrocarbon molecules having # or more carbon atoms. Accordingly, the term "C6+ hydrocarbons" is meant to describe a mixture of hydrocarbons having 6 or more carbon atoms.

The feed stream comprising C6+ hydrocarbons can be a stream obtained by first stage hydrogenation of a pyrolysis gasoline followed by fractionation of the effluent to obtain a C6-C8 cut and second stage hydrogenation of the C6-C8 cut. Preferably, the feed stream comprising C6+ hydrocarbons is a first stage hydro-treated pyrolysis gasoline. More preferably, the feed stream is a first stage hydro-treated pyrolysis gasoline from which C5– hydrocarbons has been removed, for example by the use of dehexanizer and depentanizer. However, any C5– hydrocarbons present in the streams collected from the separation system (first and second condensed light streams) can easily be removed in the subsequent benzene extraction process that recovers high purity benzene from the C6 fraction and produces a raffinate that will also contain the C5– hydrocarbons still present. Accordingly, the feed stream comprising C6+ hydrocarbons preferably comprises at most 20 w %, for example at most 10 wt %, at most 5 wt %, at most 3 wt %, at most 1 wt %, at most 0.1 wt % or at most 0.01 wt % of C5– hydrocarbons.

Preferably, the first (condensed) light stream comprising C6– hydrocarbons substantially consists of C6– hydrocarbons. The first (condensed) light stream preferably comprises at most 1 wt %, for example at most 0.5 wt % or at most 0.1 wt % of C7+ hydrocarbons. In particular, the first (condensed) light stream preferably comprises at most 500 parts per million (ppm) of toluene and at most 600 ppm of methyl cyclo hexane.

More preferably, the first (condensed) light stream preferably comprises at most 300 ppm, more preferably at most 100 ppm, more preferably at most 50 ppm, more preferably at most 10 ppm, of toluene, and/or at most 300 ppm, more preferably at most 100 ppm, more preferably at most 50 ppm, more preferably at most 10 ppm, of methyl cyclo hexane.

Preferably, the second (condensed) light stream comprising C6– hydrocarbons substantially consists of C6– hydrocarbons. The second (condensed) light stream preferably comprises at most 1 wt %, for example at most 0.5 wt % or at most 0.1 wt % of C7+ hydrocarbons. In particular, the second (condensed) light stream preferably comprises at most 500 ppm of toluene and at most 600 ppm of methyl cyclo hexane. More preferably, the second (condensed) light stream preferably comprises at most 300 ppm, more preferably at most 100 ppm, more preferably at most 50 ppm, more preferably at most 10 ppm, of toluene, and/or at most 300 ppm, more preferably at most 100 ppm, more preferably at most 50 ppm, more preferably at most 10 ppm, of methyl cyclo hexane.

Preferably, the first (boiled) heavy stream comprising C7+ hydrocarbons mainly comprises or substantially consists of C7+ hydrocarbons. The first (boiled) heavy stream preferably comprises at most 20 w %, for example at most 10 wt % or at most 5 wt % of C6– hydrocarbons. In some embodiments (for example in the first embodiment described elsewhere) wherein part of the first (boiled) heavy stream is collected from the separation system, the first (boiled) heavy stream preferably comprises at most 3 wt % of C6– hydrocarbons, in particular at most 2 wt % of benzene. In some embodiments (for example in the second embodiment described elsewhere) wherein part of the first (boiled) heavy stream is fed to the second distillation column, the first (boiled) heavy stream may comprise a higher amount of C6– hydrocarbons, for example at most 50 wt %, for example at most 40 wt %, at most 30 wt %, at most 20 w %, at most 10 wt % or at most 5 wt % of C6– hydrocarbons.

Preferably, the second (boiled) heavy stream comprising C7+ hydrocarbons substantially consists of C7+ hydrocarbons. The second (boiled) heavy stream preferably comprises at most 3 wt % of C6– hydrocarbons, in particular at most 2 wt % of benzene.

Preferably, the separation system according to the invention comprises a first vessel (V-221; V-321) and a first pump (P-221; P-321) between the first condenser and the first distillation column for storing and transferring the first condensed light stream (208,204; 305,306).

Preferably, the separation system according to the invention comprises a second vessel (V-222; V-322) and a second pump (P-222; P-322) between the second condenser and the second distillation column for storing and transferring the second condensed light stream (226,222; 315,316).

A first output stream (224) exiting the heat exchanger (H-222; H-322) can pass through the second vessel (V-222; V-322) forming a second output stream (225; 313) before passing through the second pump (P-222; P-322). A third output stream (231; 314) can join with the second condensed light stream (226,222; 315,316).

The method disclosed herein has two main groups of embodiments as described below, depending on whether the feed stream is fed to both the first distillation column and the second distillation column or only to the first distillation column.

In a first embodiment of the invention, step a) involves a1) feeding the feed stream (201) partly (202) to the first distillation column (C-221) and partly (203) to the second distillation column (C-222) and collecting a part (210) of the first heavy stream from the separation system. In this embodiment, the first and the second distillation columns operate in parallel. The feed stream is split over the two distillation columns to allow the heat available from the second condenser to match the heat requirement by the first reboiler. Both distillation columns take a fraction of the feed stream and both produce a light stream according to desired specifications and a heavy stream according to desired specifications. It was calculated that the method of this embodiment saves approximately 50% of the heat input, compared to the state of the art.

In a second embodiment, step a) involves a2) feeding the feed stream (301) to the first distillation column (C-321) and feeding a part (309) of the first heavy stream to the second distillation column (C-322). In this embodiment, the feed stream is fed to the first distillation column, which produces a light stream according to desired specifications. Before feeding to the second distillation column (C-322), the feed stream 309 is passed through a third pump (P-323) and output as feed stream (310), which is fed to the second distillation column (C-322). The heavy stream from the first distillation column is not according to desired specifications and still may contain a substantial amount of C6− hydrocarbons. A part of this stream is increased in pressure by a pump and then fed to the second distillation column that produces a light stream according to desired specifications and a heavy stream according to desired specifications. The amount and the composition of the first heavy stream (309) to be fed to the second distillation column influence the amount of heat released by the second condenser. For example, when the first heavy stream (309) to be fed to the second distillation column contains a large amount of C6− hydrocarbons, the amount of the second light stream will be large and the amount of heat released by the second condenser will be large. The amount and the composition of the first heavy stream (309) to be fed to the second distillation column are chosen such that the heat available from the second condenser matches the heat requirement by the first reboiler. It was calculated that the method of this embodiment saves approximately 50% of the heat input, compared to the state of the art.

The second condenser should desirably have a temperature higher than the temperature of the first reboiler, preferably at least 1° C. higher, more preferably at least 5° C. higher, more preferably 10° C. higher. A larger temperature difference results in a smaller size of the heat exchanger, which is economically beneficial.

In some modifications of the first and the second embodiments, the separation system further comprises a third reboiler (H-224; H-324) for reboiling a part of the first heavy stream to produce a third boiled heavy stream. Preferably, the method comprises feeding back the third boiled heavy stream to the first distillation column. This reduces the flow of the first heavy stream to the first reboiler, which reduces the energy required for the first reboiler to reboil the first heavy stream.

In some modifications of the first and the second embodiments, the separation system further comprises a third condenser (H-225; H-325) between the second condenser and the second vessel. This reduces the energy required for the second condenser to condense the second light stream. This may be advantageous when the amount of the second light stream is large. For example, in the second embodiment, if the first heavy stream comprises a high amount of C6− hydrocarbons, the amount of the second light stream will be large. The presence of the third condenser (H-325) assists the second condenser in condensing the large amount of the second light stream.

In some modifications of the second embodiment, the method further comprises the step of feeding a part of the second condensed light stream to the first distillation column. By this step, a part of the condensed light stream from the second distillation column is fed back to the first distillation column. This reduces the flow of the second condensed light stream back to the second distillation column, which in turn reduces the flow of the second light stream to the second condenser. This reduces the heat released by the second condenser and the heat taken by the first reboiler. Hence, a further control of the heat exchange balance is achieved as well as a control over the mass balance.

In some modifications of the second embodiment, the method further comprises the step of feeding a part of the first condensed light stream to the second distillation column. By this step, a part of the condensed light stream from the first distillation column is fed to the second distillation column. This increases the flow of the first light stream to the second condenser. This increases the heat released by the second condenser and the heat taken by the first reboiler. Hence, a further control of the heat exchange balance is achieved as well as a control over the mass balance.

Figure 2:
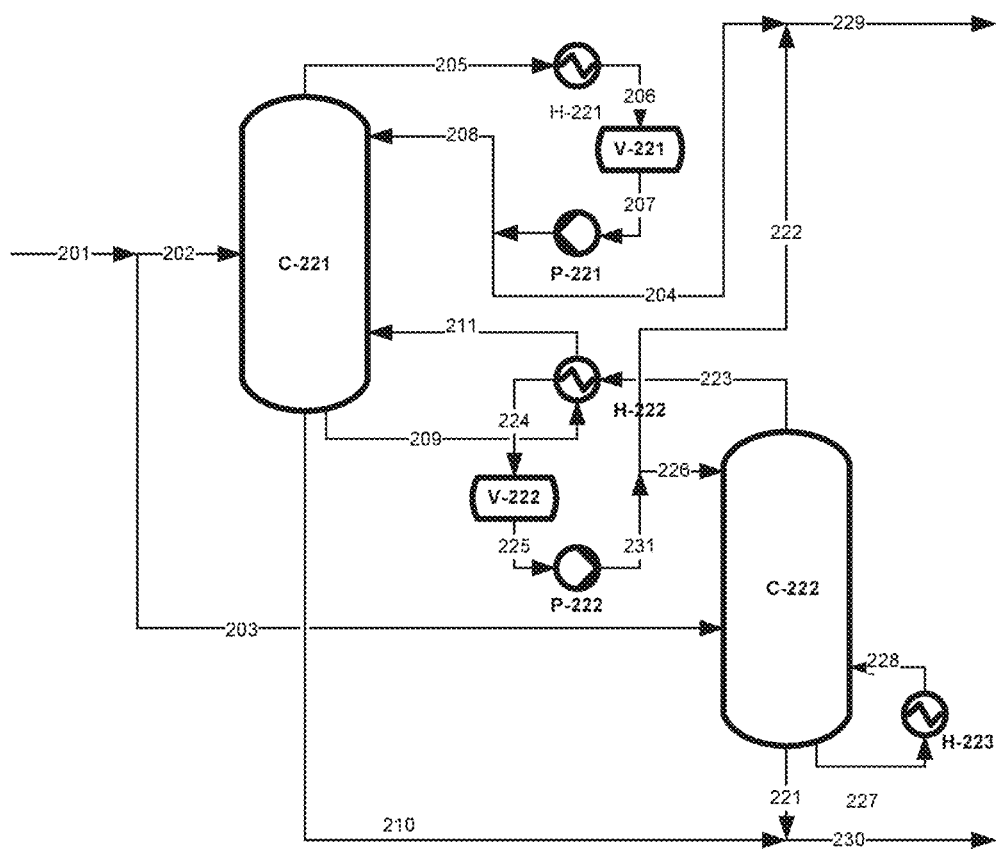
FIG. 2 schematically illustrates a first embodiment of the separation system according to the method disclosed herein.

In FIG. 2, a first embodiment of the separation system according to the invention is shown. The separation system comprises a first distillation column (C-221) for producing a first light stream (205) and a first heavy stream (209,210). The first distillation column has the lowest pressure at the top of the column and the highest pressure at the bottom of the column.

The separation system further comprises a second distillation column (C-222) for producing a second light stream (223) and a second heavy stream (221,227). The second distillation column has the lowest pressure at the top of the column and the highest pressure at the bottom of the column. The lowest pressure of the second distillation column is higher than highest pressure of the first distillation column.

The feed stream (201) is fed partly (202) to the first distillation column (C-221) and partly (203) to the second distillation column (C-222).

The feed stream (202) fed to the first distillation column (C-221) is separated into a light stream (205) and a heavy stream (209,210).

The first light stream (205) is passed onto an arrangement of a first condenser (H-221), a first vessel (V-221) and a first pump (P-221), which condenses the first light stream (205) to produce a first condensed light stream (208,204). A part (208) of the first condensed light stream is fed back to the first distillation column (C-221) as reflux. A part (204) of the first condensed light stream is collected from the separation system.

A part (210) of the first heavy stream is collected from the separation system.

The feed stream (203) fed to the second distillation column (C-222) is separated into a second light stream (223) and a second heavy stream (221,227).

A part (221) of the second heavy stream is collected from the separation system. A part (227) of the second heavy stream is fed to a second reboiler (H-223) to produce a second boiled heavy stream (211), which is fed back to the second distillation column (C-222).

The system further comprises a heat exchanger (H-222) comprising a first reboiler for boiling a part (209) of the first heavy stream to produce a first boiled heavy stream (211) and a second condenser for condensing the second light stream (223) to produce a second condensed light stream (226,222). The heat exchanger (H-222) is arranged such that heat released from the second condenser is used as heat for the first reboiler. This substantially reduces the overall energy consumption of the system. Accordingly, a part (209) of the first heavy stream is fed to a first reboiler of a heat exchanger (H-222) to produce a first boiled heavy stream (211), which is fed back to the first distillation column (C-221). The second light stream (223) is passed onto an arrangement of a second condenser of the heat exchanger (H-222), a second vessel (V-222) and a second pump (P-222), which condenses the second light stream (223) to produce a second condensed light stream (226,222). A part (226) of the second condensed light stream is fed back to the second distillation column (C-222) as reflux. A part (222) of the second condensed light stream is collected from the separation system.

The first condensed light stream and the second condensed light stream collected from the separation system is indicated as stream 229. The stream 229 preferably comprises at most 500 ppm of toluene and at most 600 ppm of methyl cyclo hexane. The first heavy stream and the second heavy stream collected from the separation system is indicated as stream 230. The stream 230 preferably comprises at most 2 wt % of benzene.

Figure 3:
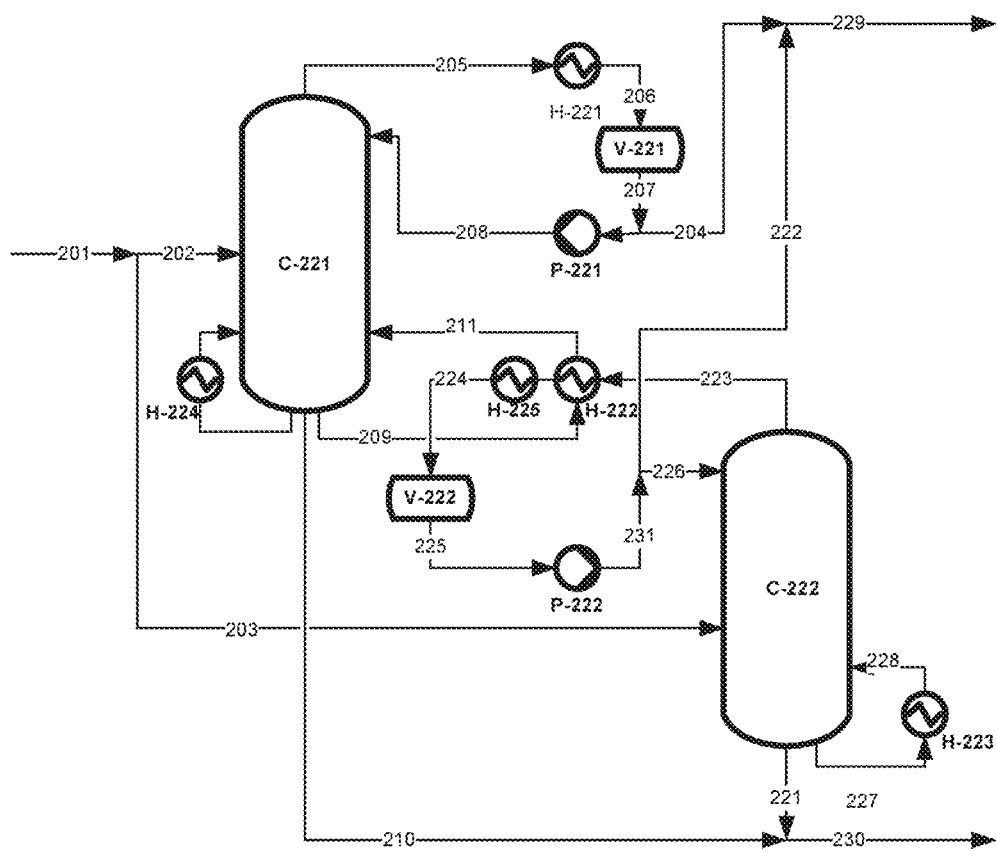
FIG. 3 schematically illustrates a modification of FIG. 2.

FIG. 3 is a modification of the first embodiment and is identical to FIG. 2 except for the following: The separation system further comprises a third reboiler (H-224) for reboiling a part of the first heavy stream to produce a third boiled heavy stream. The third boiled heavy stream is fed back to the first distillation column (C-221). The separation system further comprises a third condenser (H-225) between the second condenser (H-222B) and the second vessel (V-222). The third reboiler (H-224) and the third condenser (H-225) allow better control of the heat balance over the system and control of the product specs. The columns can be independently controlled through this arrangement.

Figure 4:
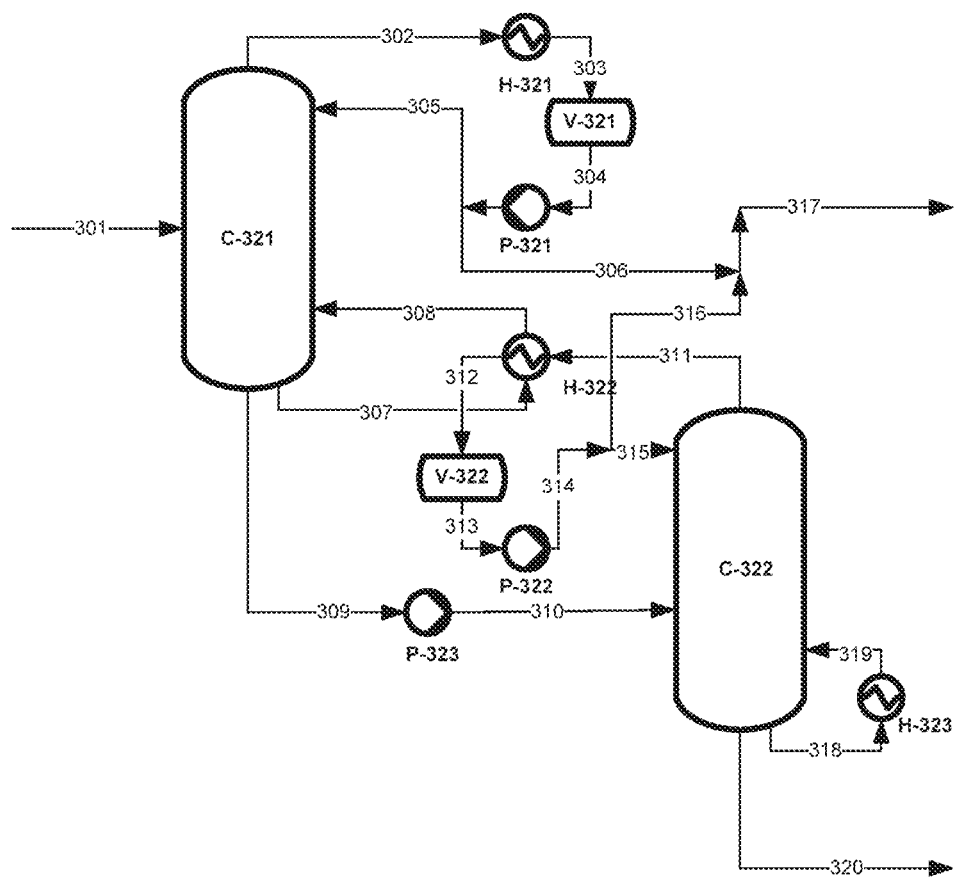
FIG. 4 schematically illustrates a second embodiment of the separation system according to the method disclosed herein.

FIG. 4 shows a second embodiment which is similar to FIG. 1 except that the method involves feeding all (301) of the feed stream to the first distillation column (C-321) and the first heavy stream is not collected but a part (309) of the first heavy stream is fed to the second distillation column (C-322) to be further separated. Accordingly, in this embodiment, the feed for the second distillation column (C-322) is the first heavy stream (309). The first heavy stream (309) may still contain some C6– hydrocarbons.

Also this system comprises a heat exchanger (H-322) comprising a first reboiler for boiling a part (307) of the first heavy stream to produce a first boiled heavy stream (308) and a second condenser for condensing the second light stream (311) to produce a second condensed light stream (315,316). The heat exchanger (H-322) is arranged such that heat released from the second condenser is used as heat for the first reboiler. The advantage of the reduction of heat consumption is achieved as in the first embodiment.

The first condensed light stream and the second condensed light stream collected from the separation system is indicated as stream 317. The stream 317 preferably comprises at most 500 ppm of toluene and at most 600 ppm of methyl cyclo hexane. The second heavy stream collected from the separation system comprises at most 2 wt % of benzene.

Figure 5:
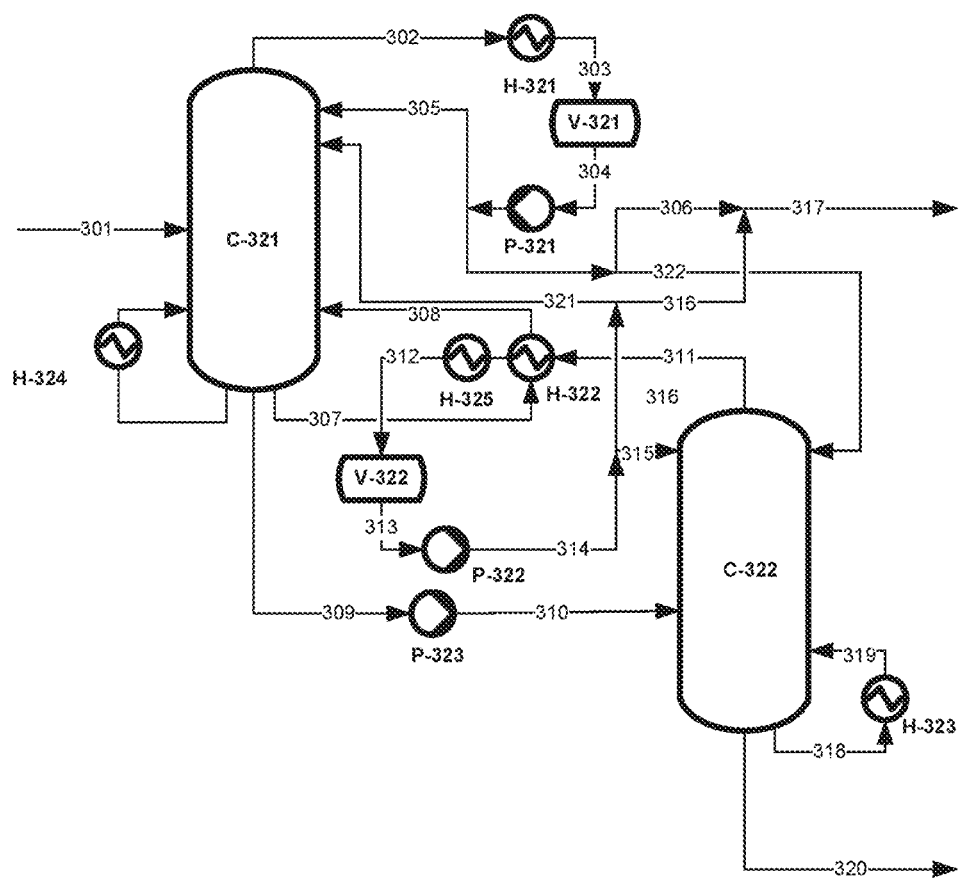
FIG. 5 schematically illustrates a modification of FIG. 4.

FIG. 5 is a modification of the second embodiment and is identical to FIG. 3 except for the following: The separation system further comprises a third reboiler (H-324) for reboiling a part of the first heavy stream to produce a third boiled heavy stream.

The third boiled heavy stream is fed back to the first distillation column (C-321). The separation system further comprises a third condenser (H-325) between the second condenser (H-322B) and the second vessel (V-322). Further, a part (321) of the second condensed light stream is fed to the first distillation column (C-321). Further, a part (322) of the first condensed light stream is fed to the second distillation column (C-322). The third reboiler (H-324) and the third condenser (H-325) allow better control of the heat balance over the system and control of the product specs. The columns can be independently controlled through this arrangement.

The following example are merely illustrative of the method disclosed herein and are not intended to limit the scope hereof. Examples of the pressure and the temperature of the first and the second condensers and the reboilers calculated for a model feed composition are shown below.

TABLE 2

Examples of first embodiment

| | First distillation column C-221 | | Heat exchanger | Second distillation column C-222 | |
|---|---|---|---|---|---|
| | First condenser pressure (bara)/ temperature (° C.) | First reboiler pressure (bara)/ temperature (° C.) | H-222 Temperature driving force (° C.)) | Second condenser pressure (bara)/ temperature (° C.) | Second reboiler pressure (bara)/ temperature (° C.) |
| Ex 1 | 0.5/52 | 0.6/104 | 7 | 2.8/111 | 3.2/172 |
| Ex 2 | 1.0/73 | 1.3/122 | 10 | 4.5/132 | 4.9/194 |
| Ex 3 | 1.3/82 | 1.6/131 | 15 | 6.0/146 | 6.4/209 |

It is generally preferable that the temperature of the second reboiler is low for the purpose of preventing fouling and allowing the use of a less expensive heating medium. It is also generally preferable that no vacuum has to be used in the system (thus, the first condenser pressure which has the lowest pressure in the system has a pressure of at least 1.0 bara).

For allowing the temperature of the second reboiler of 172° C. and the temperature difference of 7° C. as in Ex 1, the first reboiler pressure is 0.6 bara and the first condenser pressure is 0.5 bara. Thus, in Ex 1, vacuum is required in the first distillation column. In Ex 2, the temperature of the second reboiler is higher than in Ex 1 although vacuum is not used.

TABLE 3

Examples of second embodiment

| | First distillation column C-321 | | Heat exchanger H-322 Temperature driving force H322 (° C.) | Second distillation column C-322 | |
|---|---|---|---|---|---|
| | Condenser pressure (bara)/ temperature (° C.) | Reboiler pressure (bara)/ temperature (° C.) | | Condenser pressure (bara)/ temperature (° C.) | Reboiler pressure (bara)/ temperature (° C.) |
| Ex 4 | 1.1/74 | 1.4/111 | 5 | 2.8/116 | 3.2/172 |
| Ex 5 | 0.5/50 | 0.7/88 | 6 | 1.6/94 | 1.9/148 |
| Ex 6 | 2.0/95 | 2.3/130 | 20 | 6.0/150 | 6.3/208 |

In this case, for allowing the temperature of the second reboiler of 172° C. and the temperature difference of 5° C. as in Ex 4, the first reboiler pressure and the first condenser pressure do not have to be very low: the first condenser pressure does not have to be lower than 1.0 bara, which is beneficial. In Ex 5, a low temperature of the second reboiler of 148° C. was allowed when the first condenser pressure was 0.5 bara.

It can therefore be seen that the second embodiment is more advantageous than the first embodiment in that the first condenser pressure can be maintained high (use of vacuum can be avoided) for the same second reboiler temperature, or a lower second reboiler temperature can be used for the same first condenser pressure.

The method disclosed herein includes at least the following embodiments:

Embodiment 1: A method for separating a feed stream comprising C6+ hydrocarbons using a separation system for separating a feed stream comprising C6+ hydrocarbons, the system comprising: A method for separating a feed stream comprising C6+ hydrocarbons using a separation system for separating a feed stream comprising C6+ hydrocarbons, the system comprises: i) a first distillation column for producing a first light stream comprising C6− hydrocarbons and a first heavy stream comprising C7+ hydrocarbons, wherein the first distillation column is operated between a lowest pressure and a highest pressure, ii) a second distillation column for producing a second light stream comprising C6− hydrocarbons and a second heavy stream comprising C7+ hydrocarbons, wherein the second distillation column is operated between a lowest pressure and a highest pressure, wherein the lowest pressure of the second distillation column is higher than the highest pressure of the highest distillation column, iii) a heat exchanger comprising a first reboiler for reboiling a part of the first heavy stream to produce a first boiled heavy stream and a second condenser for condensing the second light stream to produce a second condensed light stream, wherein the first reboiler and the second condenser are arranged such that heat released from the second condenser is used as heat for the first reboiler, iv) a first condenser for cooling the first light stream to produce a first condensed light stream and v) a second reboiler for reboiling a part of the second heavy stream to produce a second boiled heavy stream, wherein the method comprises the steps of: a) a2) feeding the feed stream to the first distillation column and feeding a part of the first heavy stream to the second distillation column, b) feeding a part of the first heavy stream to the first reboiler and feeding back the first boiled heavy stream to the first distillation column, c) feeding the second light stream to the second condenser and feeding back a part of the second light stream to the second distillation column as reflux and collecting a part of the second condensed light stream from the separation system, d) feeding the first light stream to the first condenser and feeding back a part of the first condensed light stream to the first distillation column as reflux, e) feeding a part of the second heavy stream to the second reboiler and feeding back the second boiled heavy stream to the second distillation column, and f) collecting a part of the first condensed light stream and a part of the second heavy stream from the separation system, wherein the first condensed light stream collected from the separation system comprises at most 500 ppm of toluene and at most 600 ppm of methyl cyclo hexane.

Embodiment 2: The method according to Embodiment 1, wherein the first condensed light stream collected from the separation system and/or the second condensed light stream collected from the separation system comprises at most 500 ppm of toluene and at most 600 ppm of methyl cyclo hexane.

Embodiment 3: The method according to any one of Embodiments 1-2, wherein the second heavy stream collected from the separation system comprises at most 2 wt % of benzene.

Embodiment 4: The method according to any one of Embodiments 1-3, wherein the separation system further comprises a third reboiler for reboiling a part of the first heavy stream to produce a third boiled heavy stream and the method comprises feeding back the third boiled heavy stream to the first distillation column.

Embodiment 5: The method according to any one of Embodiments 1-4, wherein the separation system further comprises a third condenser between the second condenser and the second vessel.

In general, the invention may alternately comprise, consist of, or consist essentially of, any appropriate components herein disclosed. The invention may additionally, or alternatively, be formulated so as to be devoid, or substantially free, of any components, materials, ingredients, adjuvants or species used in the prior art compositions or that are otherwise not necessary to the achievement of the function and/or objectives of the present invention. The endpoints of all ranges directed to the same component or property are inclusive and independently combinable (e.g., ranges of "less than or equal to 25 wt %, or 5 wt % to 20 wt %," is inclusive of the endpoints and all intermediate values of the ranges of "5 wt % to 25 wt %," etc.). Disclosure of a narrower range or more specific group in addition to a broader range is not a disclaimer of the broader range or larger group. "Combination" is inclusive of blends, mixtures, alloys, reaction products, and the like. Furthermore, the terms "first," "second," and the like, herein do not denote any order, quantity, or importance, but rather are used to denote one element from another. The terms "a" and "an" and "the" herein do not denote a limitation of quantity, and are to be construed to cover both the singular and the plural, unless otherwise indicated herein or clearly contradicted by context. "Or" means "and/or." The suffix "(s)" as used herein is intended to include both the singular and the plural of the term that it modifies, thereby including one or more of that term (e.g., the film(s) includes one or more films). Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments.

The modifier "about" used in connection with a quantity is inclusive of the stated value and has the meaning dictated by the context (e.g., includes the degree of error associated with measurement of the particular quantity). The notation "+10%" means that the indicated measurement can be from an amount that is minus 10% to an amount that is plus 10% of the stated value. The terms "front", "back", "bottom", and/or "top" are used herein, unless otherwise noted, merely for convenience of description, and are not limited to any one position or spatial orientation. "Optional" or "optionally" means that the subsequently described event or circumstance can or cannot occur, and that the description includes instances where the event occurs and instances where it does not. Unless defined otherwise, technical and scientific terms used herein have the same meaning as is commonly understood by one of skill in the art to which this invention belongs. A "combination" is inclusive of blends, mixtures, alloys, reaction products, and the like.

It is noted that the invention relates to all possible combinations of features described herein, preferred in particular are those combinations of features that are present in the claims. It will therefore be appreciated that all combinations of features relating to the composition according to the invention; all combinations of features relating to the process according to the invention and all combinations of features relating to the composition according to the invention and features relating to the process according to the invention are described herein.

It is further noted that the term 'comprising' does not exclude the presence of other elements. However, it is also to be understood that a description on a product/composition comprising certain components also discloses a product/composition consisting of these components. The product/composition consisting of these components may be advantageous in that it offers a simpler, more economical process for the preparation of the product/composition. Similarly, it is also to be understood that a description on a process comprising certain steps also discloses a process consisting of these steps. The process consisting of these steps may be advantageous in that it offers a simpler, more economical process.

When values are mentioned for a lower limit and an upper limit for a parameter, ranges made by the combinations of the values of the lower limit and the values of the upper limit are also understood to be disclosed.

All cited patents, patent applications, and other references are incorporated herein by reference in their entirety. However, if a term in the present application contradicts or conflicts with a term in the incorporated reference, the term from the present application takes precedence over the conflicting term from the incorporated reference. While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications, variations, improvements, and substantial equivalents.

What is claimed is:

1. A method for separating a feed stream comprising C6+ hydrocarbons using a separation system for separating a feed stream comprising C6+ hydrocarbons, the system comprising:

i) a first distillation column for producing a first light stream comprising C6− hydrocarbons and a first heavy stream comprising C7+ hydrocarbons, wherein the first distillation column is operated between a lowest pressure and a highest pressure,
ii) a second distillation column for producing a second light stream comprising C6− hydrocarbons and a second heavy stream comprising C7+ hydrocarbons, wherein the second distillation column is operated between a lowest pressure and a highest pressure, wherein the lowest pressure of the second distillation column is higher than the highest pressure of the first distillation column,
iii) a heat exchanger comprising a first reboiler for reboiling a part of the first heavy stream to produce a first boiled heavy stream and a second condenser for condensing the second light stream to produce a second condensed light stream, wherein the first reboiler and the second condenser are arranged such that heat released from the second condenser is used as heat for the first reboiler,
iv) a first condenser for cooling the first light stream to produce a first condensed light stream and
v) a second reboiler for reboiling a part of the second heavy stream to produce a second boiled heavy stream, wherein the method comprises the steps of:
a) feeding the feed stream to the first distillation column and feeding a part of the first heavy stream to the second distillation column,
b) feeding a part of the first heavy stream to the first reboiler and feeding back the first boiled heavy stream to the first distillation column,
c) feeding the second light stream to the second condenser and feeding back a part of the second condensed light stream to the second distillation column as reflux and collecting a part of the second condensed light stream from the separation system,
d) feeding the first light stream to the first condenser and feeding back a part of the first condensed light stream to the first distillation column as reflux,
e) feeding a part of the second heavy stream to the second reboiler and feeding back the second boiled heavy stream to the second distillation column, and
f) collecting a part of the first condensed light stream and a part of the second heavy stream from the separation system,
wherein the first condensed light stream collected from the separation system comprises at most 500 ppm of toluene and at most 600 ppm of methyl cyclo hexane, and
wherein
the first condenser is operated between a lowest pressure of 0.5 bara and a highest pressure of 2.0 bara,
the second condenser is operated between a lowest pressure of 1.6 bara and a highest pressure of 6.0 bara,
the first condenser is operated between a lowest temperature of 52° C. and a highest temperature of 95° C.,
the second condenser is operated between a lowest temperature of 94° C. and a highest temperature of 150° C.,
the first reboiler is operated between a lowest pressure of 0.6 bara and a highest pressure of 2.3 bara,
the second reboiler is operated between a lowest pressure of 1.9 bara and a highest pressure of 6.4 bara, the first reboiler is operated between a lowest temperature of 88° C. and a highest temperature of 131° C., and the second reboiler is operated between a lowest temperature of 148° C. and a highest temperature of 209° C.

2. The method according to claim 1, wherein the second condensed light stream collected from the separation system comprises at most 500 ppm of toluene and at most 600 ppm of methyl cyclo hexane.

3. The method according to claim 1, wherein the second heavy stream collected from the separation system comprises at most 2 wt % of benzene.

4. The method according to claim 1, wherein the separation system further comprises a third reboiler for reboiling a part of the first heavy stream to produce a third boiled heavy stream and the method comprises feeding back the third boiled heavy stream to the first distillation column.

5. The method according to claim 1, wherein the separation system further comprises a third condenser between the second condenser and the second vessel.

6. The method according to claim 1, wherein the feed stream comprises at most 20 w % C5− hydrocarbons.

7. The method according to claim 1, wherein the feed stream comprises at most 10 w % C5− hydrocarbons.

8. The method according to claim 1, wherein the second light stream comprising C6− hydrocarbons comprises at most 1 wt % of C7+ hydrocarbons.

9. The method according to claim 1, wherein the first light stream comprising C6− hydrocarbons comprises at most 1 wt % of C7+ hydrocarbons.

10. The method according to claim 1, wherein the first heavy stream comprising C7+ hydrocarbons comprises at most 20 w % of C6− hydrocarbons.

11. The method according to claim 1, wherein the first heavy stream comprising C7+ hydrocarbons comprises at most 10 w % of C6− hydrocarbons.

12. The method according to claim 1, wherein the first heavy stream comprising C7+ hydrocarbons comprises at most 5 w % of C6− hydrocarbons.

13. The method according to claim 1, wherein the second heavy stream comprising C7+ hydrocarbons comprises at most 3 wt % of C6− hydrocarbons.

14. The method according to claim 1, wherein the second heavy stream comprising C7+ hydrocarbons comprises at most 2 wt % of C6− hydrocarbons.

15. The method according to claim 1, wherein
the first light stream comprising C6− hydrocarbons comprises at most 1 wt % of C7+ hydrocarbons,
the first heavy stream comprising C7+ hydrocarbons comprises at most 20 w % of C6− hydrocarbons, and
the second heavy stream comprising C7+ hydrocarbons comprises at most 3 wt % of C6− hydrocarbons.

16. The method according to claim 1, wherein the method further comprises combining the first condensed light stream and the second condensed light stream.

17. The method according to claim 1, wherein the method further comprises collecting the first heavy stream.

18. The method according to claim 1, wherein the method further comprises combining the first heavy stream and the second heavy stream.

19. The method according to claim 1, wherein the method further comprises combining the first condensed light stream and the second condensed light stream;
collecting the first heavy stream; and
combining the first heavy stream and the second heavy stream.

* * * * *